United States Patent [19]

Abbott et al.

[11] Patent Number: 4,578,990

[45] Date of Patent: Apr. 1, 1986

[54] DIFFERENTIAL PRESSURE CAPILLARY VISCOMETER FOR MEASURING VISCOSITY INDEPENDENT OF FLOW RATE AND TEMPERATURE FLUCTUATIONS

[75] Inventors: Scot D. Abbott; Wallace W. Yau, both of Wilmington, Del.

[73] Assignee: E. I. Du Pont de Nemours and Company, Wilmington, Del.

[21] Appl. No.: 669,017

[22] Filed: Nov. 7, 1984

[51] Int. Cl.$^4$ .............................. G01N 11/04
[52] U.S. Cl. ..................... 73/55; 73/61.1 C
[58] Field of Search ............... 73/55, 54, 61.1 C, 56

[56] References Cited

U.S. PATENT DOCUMENTS

| | | | |
|---|---|---|---|
| 3,540,264 | 11/1970 | Cerrutti et al. | 73/55 |
| 3,548,638 | 12/1970 | Uchida et al. | 73/55 |
| 3,808,877 | 5/1974 | Blair | 73/55 |
| 3,837,217 | 9/1974 | Schulz | 73/61.1 |
| 3,924,448 | 12/1975 | Howard et al. | 73/55 |
| 3,938,369 | 2/1976 | de Bok | 73/55 |
| 3,962,907 | 6/1976 | Peyrouset et al. | 73/55 |
| 4,184,364 | 1/1980 | Du Bae | 73/54 |
| 4,241,602 | 12/1980 | Han et al. | 73/56 |
| 4,258,564 | 3/1981 | Hulme et al. | 73/61.1 C |
| 4,286,457 | 9/1981 | Johnson | 73/53 |
| 4,309,898 | 1/1982 | Horton | 73/23.1 |
| 4,316,383 | 2/1982 | Fruman et al. | 73/55 |
| 4,350,285 | 9/1982 | Holben | 236/1 R |
| 4,384,472 | 5/1983 | Tournier | 73/30 |
| 4,403,503 | 9/1983 | Banerjee et al. | 73/61.1 |
| 4,425,790 | 1/1984 | Bice et al. | 73/55 |
| 4,463,598 | 8/1984 | Haney | 73/55 |
| 4,478,071 | 10/1984 | Lecacheux et al. | 73/55 |

OTHER PUBLICATIONS

Ouano-J. Polym. Sci., Part A-1, 10, 2169 (1972).

*Primary Examiner*—Stewart J. Levy
*Assistant Examiner*—Hezron E. Williams
*Attorney, Agent, or Firm*—Hilmar L. Fricke

[57] ABSTRACT

A means for measuring either the intrinsic or inherent viscosity of a solute in solution with a solvent which is independent of flow rate and temperature fluctuations. The solution is passed through one capillary tube and the solvent through a second capillary, and the pressure drop across each is measured. Signals corresponding to each pressure drop measurement are fed to a logarithmic amplification means where they are processed to determine either the intrinsic or inherent viscosity of the solute independent of flow rate and temperature fluctuations. The viscosity measuring means may also be used together with size exclusion chromatography to determine the molecular weight distribution of polymer materials. It may also be used to measure the relative viscosity of a sample liquid and a reference liquid, and to determine the viscosity of the sample liquid independent of flow rate and temperature fluctuations.

25 Claims, 6 Drawing Figures

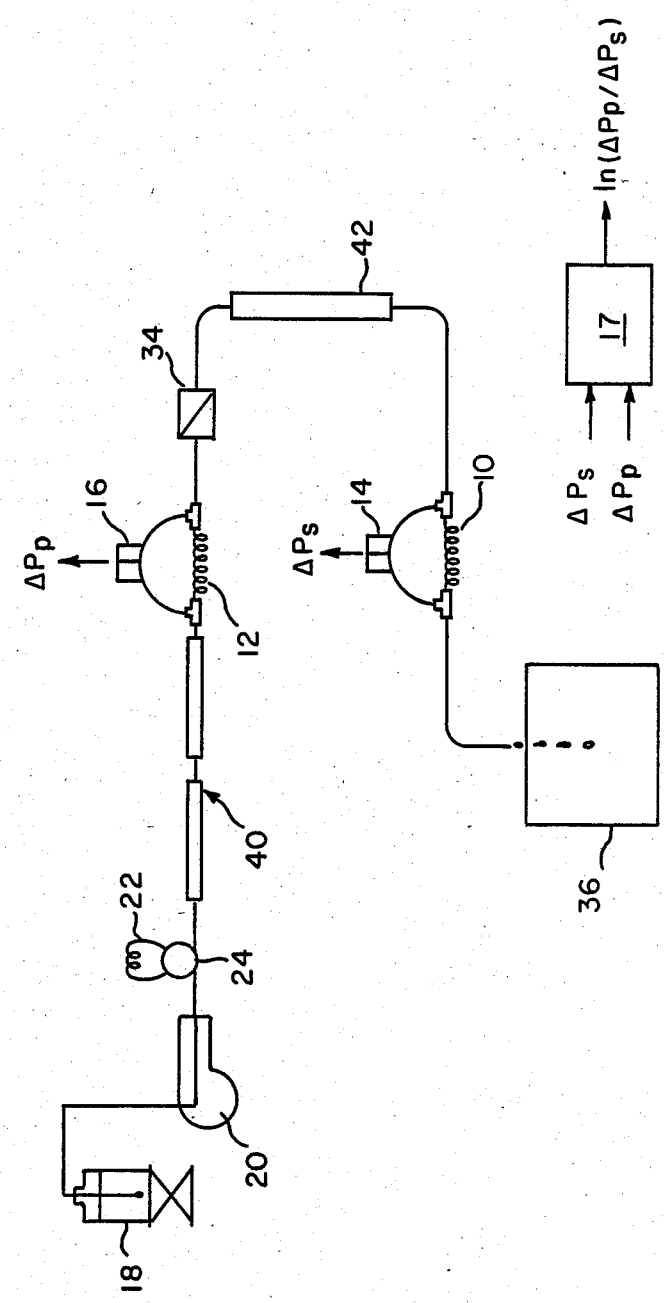

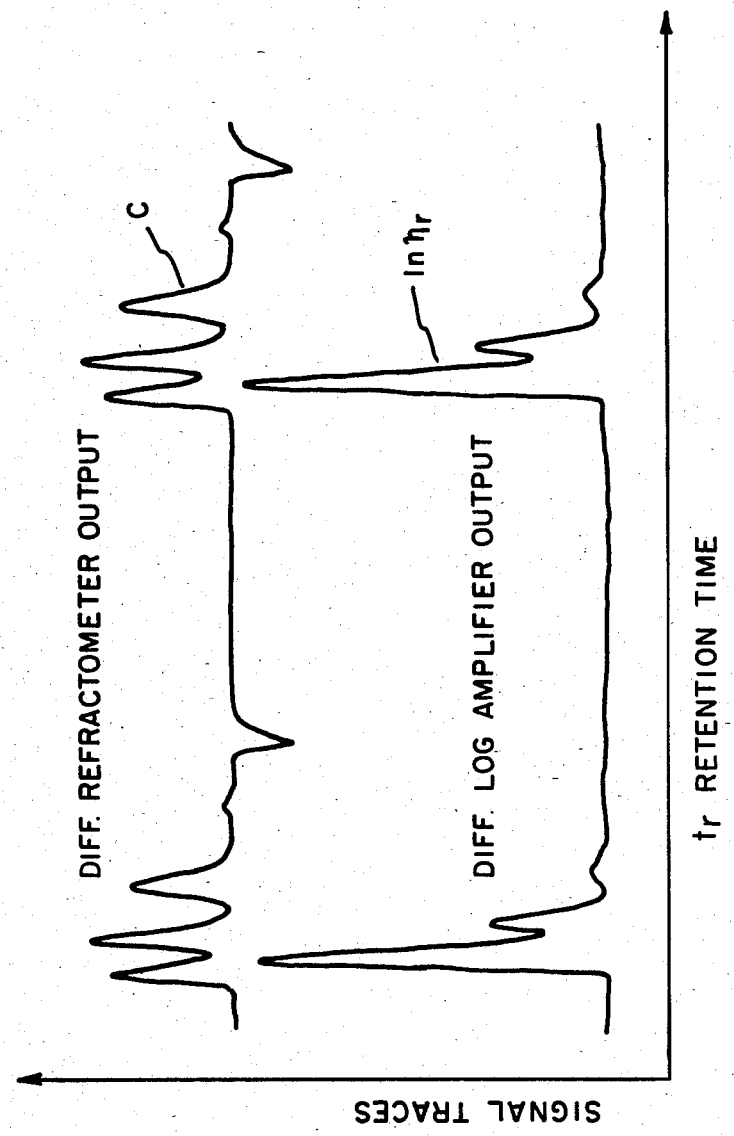

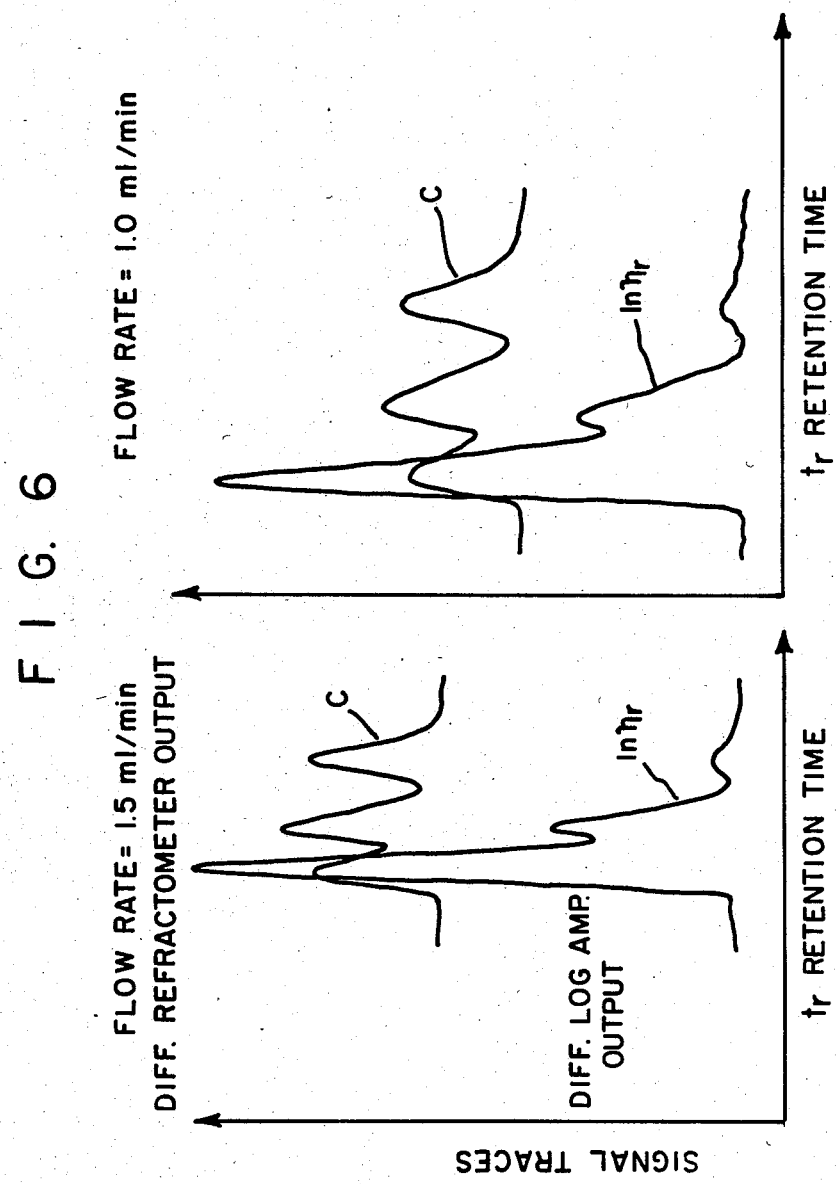

DIFFERENTIAL PRESSURE CAPILLARY VISCOMETER FOR MEASURING VISCOSITY INDEPENDENT OF FLOW RATE AND TEMPERATURE FLUCTUATIONS

BACKGROUND OF THE INVENTION

1. Field of the Invention

This invention relates to capillary viscometers. More specifically, it relates to differential pressure capillary viscometers which may be used alone to measure the viscosity of fluids or together with a chromatograph to obtain accurate viscosity information for determining molecular weight distributions.

2. Discussion of the Prior Art

Accurate measurements of fluid viscosity are important in many industries. A capillary viscometer is often used to measure the absolute viscosity of a given fluid. For many purposes, however, it is necessary to know the relative viscosity of two fluids. Relative viscosity is often determined experimentally by measuring the absolute viscosity of each fluid separately with a capillary viscometer and then calculating the ratio.

Relative viscosity is of particular importance in polymer research and manufacturing since it can be used to measure molecular weights and to determine molecular weight distributions, which provide important information relating to the physical properties of polymers. A comparison of the viscosity behavior of two polymers of the same molecular weight, for example, is used as a measure of the degree of branching. One of the oldest means used to obtain such information is to measure the viscosity of a known concentration of a polymer in a solvent. By utilizing the ratio of the viscosity of the polymer-solvent solution, $\eta_p$, to that of the pure solvent, $\eta_s$, the intrinsic viscosity $[\eta]$ of the polymer can be calculated in accordance with following mathematical relationship:

Relative viscosity $\eta_r = \eta_p/\eta_s$
Specific viscosity $\eta_{sp} = \eta_r - 1$
Inherent viscosity $\eta_{inh} = (\ln \eta_r)/C$
(where C is the polymer weight concentration and ln is the symbol for natural logarithm)
and finally $$[\eta] = \lim_{c \to 0} \eta_{inh} = \lim_{c \to 0} \eta_{sp}/C$$
$$= \lim_{c \to 0} (\ln \eta_r)/C$$

(where $$\lim_{c \to 0}$$

is the mathematical symbol meaning limit of the quantity when the concentration C approaches zero)

Inherent and intrinsic viscosities are important polymer characterization parameters. The intrinsic viscosity, for example, provides an indication of the size of the polymer molecules. The value of $[\eta]$ is not a function of polymer concentration or the viscosity of the solvent medium. The value of $[\eta]$ for a linear polymer in a specific solvent is related to the polymer molecular weight M through the Mark-Houwink Equation:

$$[\eta] = KM^\alpha$$

where K and $\alpha$ are Mark-Houwink viscosity constants, some of which are available in polymer handbooks.

Prior art viscometers have been designed to measure viscosities in a number of ways. An early device used a single capillary of known diameter and length. Both the volume rate of flow of the solution and the pressure drop for flow through the capillary are measured. The pressure drop is usually measured by an electrical signal generated by a pressure transducer. The various viscosities are then calculated from the known geometrical parameters of the capillary.

These types of prior art viscometers have proved to be inaccurate because of signal-to-noise problems in the signal generated by the pressure transducer. Part of this problem is due to high frequency pumping noise and back pressure fluctuations. The former is caused by the reciprocating action of the high frequency pumps commonly used to move solvent and polymer solution through the viscometer. Back pressure fluctuations cause flow rate fluctuations and occur when the sample solution goes through various high resistant elements such as end-frits, valves, connectors and the capillary tube itself.

A significant part of this problem is due to actual flow rate fluctuations. These can occur for a number of reasons such as whenever the polymer sample is injected into the solvent stream. Sample injection upsets the flow rate, and noise is generated which hinders accurate viscosity measurement. Accordingly, measuring viscosity independent of flow rate fluctuations is critical to accurate viscosity readings.

Viscosity measurements are also very sensitive to temperature fluctuations. These can occur when the temperature of the solvent supply is not controlled carefully and is affected by environmental temperature changes. Sample injection can also cause temperature upsets. Measuring viscosity independent of temperature fluctuations is therefore important in obtaining accurate viscosity measurements.

An improved viscometer described in U.S. Pat. No. 3,808,877, granted May 7, 1974, to David E. Blair and assigned to the same assignee as the present application, sought to solve some of these problems. The Blair viscometer used a flow restrictor between the solvent supply and capillary to try to maintain the flow rates constant. Also, it measured relative viscosity by taking separate pressure drop measurements, first when polymer solution and then when pure solvent flowed through the capillary. In its preferred embodiment, two capillary tubes were arranged in parallel, one filled with polymer solution and the other only with solvent. In another version, the two tubes were connected in series, with pure solvent flowing through one and polymer solution through the other, and the pressure drop across each was measured. In each case, the capillary tubes had to be exactly matched so as to be identical in diameter and length. Otherwise, the pressure drops across both would not be equal for a given flow rate. If, however, the capillaries were not maintained at the identical temperature, they became "unmatched" in pressure drop, which resulted in lower sensitivity. Fluctuations in flow rate as well as temperature also adversely affected the accuracy of Blair's relative viscosity measurements.

A capillary viscometer which is similar to Blair's preferred parallel arrangement for measuring the differential pressure across a capillary bridge is described in U.S. Pat. No. 4,463,598 granted Aug. 7, 1984, to Max A.

Haney. This device, as in the case of Blair's, requires the capillaries to be matched. Also, Haney, like Blair, does not compensate for flow rate and temperature fluctuations in real time when it measures the differential pressure drops. Consequently, neither Blair nor Haney provides viscosity measurements independent of flow rate and temperature fluctuations.

A more accurate viscometer is also needed in size exclusion chromatography (SEC) such as gel permeation chromatography (GPC) analysis. This technique has become widely used because of its ability to separate polymeric materials in a dilute solution according to molecular size. It utilizes columns containing porous packings which are capable of separating the molecules in a multicomponent polymer sample according to their size. The polymer components migrate through the column at different velocities and elute separately from the column at different times. The largest polymer molecules elute first and the smallest molecules last. By detecting the amount of polymer fractions in the eluant, a GPC elution curve is generated which reflects the molecular weight distribution of the multicomponent polymer sample.

In a GPC device, a detector is commonly used for providing the weight concentration profile of the elution curve. The polymer sample concentration profile is commonly obtained by using a differential refractometer. Molecular weight information is provided indirectly by the time of elution (also referred to as retention time) of the different polymer components in the sample. By using standardized correlations, which are often not available, the molecular weight distribution of the polymer sample could be calculated.

One major drawback with this type of instrument is that it does not directly measure the molecular weight of polymer molecules as they elute from the GPC colums. Also, there is no calibration of the GPC peak retention times with the polymer molecular weight. Rather, it is necessary to assume some relationship between retention times and molecular weights over a wide range of different polymer structures. Quite obviously, a detector which will provide a means for measuring molecular weight directly is preferable.

A continuous capillary type viscometer was proposed for GPC analysis by A. C. Ouano in J. Polym. Sci. Part A-1, 10 2169 (1972). A single capillary tube was placed in series with a concentration detector such as a differential refractometer at the exit end of the GPC column. As liquid continuously flowed through the capillary, the pressure drop across the capillary was measured and recorded. When a polymer solution of higher viscosity than the solvent reached the capillary, a peak in the $\Delta P$ recording trace was detected. Variations of this type of GPC-viscosity detector are described in U.S. Pat. No. 3,837,217, granted Sept. 24, 1974, to W. W. Schulz and U.S. Pat. No. 4,286,457, granted Sept. 1, 1981, to H. W. Johnson.

These GPC-viscosity detectors, however, remain inaccurate because the pressure drop $\Delta P$ signals are still subject to flow rate and temperature fluctuations. While the improvements described in Blair in U.S. Pat. No. 3,808,877 might help somewhat in GPC analysis as suggested by Haney in U.S. Pat. No. 4,463,598, there remains a need for an accurate means for measuring viscosity which is truly independent of fluctuations in flow rate and temperature. The present invention overcomes the problems associated with the prior art devices by eliminating the need for matched capillaries and by eliminating the dependence of the relative viscosity measurement on fluctuations in flow rate and temperature.

SUMMARY OF THE INVENTION

The present invention provides a means for measuring either the intrinsic or inherent viscosity of a solute in solution with a solvent by a process which is independent of flow rate and temperature fluctuations comprising the steps of:
  passing the solvent through a first capillary tube,
  passing the solution through a second capillary tube connected in series with the first capillary tube,
  measuring separately the pressure drop across the first and second capillary tubes when each is full of flowing solvent and solution, respectively,
  generating signals corresponding to the pressure drop across each capillary tube, and
  employing said signals to measure either the intrinsic or inherent viscosity of the solute by use of logarithmic amplification wherein the viscosity measured is independent of flow rate and temperature fluctuations.

An apparatus for accomplishing this process comprises in combination:
  a first capillary tube through which the solvent flows,
  a second capillary tube arranged in series with the first capillary tube and through which the solution flows,
  solvent supply means for supplying solvent to flow through both capillary tubes,
  solution supply means for supplying a sample of the solute to the solvent stream so that solution flows through the second capillary tube,
  means for measuring the pressure drop across each capillary tube and generating a signal responsive to each pressure drop, and
  logarithmic amplification means for receiving and processing the pressure drop signals for use in measuring either the intrinsic or inherent viscosity of the solute independent of the flow rate and temperature fluctuations of the solution and the solvent.

The invention may also be employed with GPC or other SEC analysis means to obtain information on the molecular weight distribution of polymer material. The invention may also be used as an in-line process monitor or as a stand-alone viscometer.

While the present invention is described herein with reference particularly to polymer-solvent solutions, it should be understood that the invention may be used with other sample and referencing liquids wherever accurate viscosity measurements are needed. Thus, the viscosity of other sample liquids may be readily calculated from the relative viscosity measurement where the viscosity of the referencing liquid is known.

The present invention utilizes two capillaries arranged in series. A pressure transducer is connected across each capillary to monitor simultaneously the pressure drop of fluid flowing through each tube. The pressure drop measured across the first, or analytical capillary, will correspond to the sample liquid, in this case, the polymer-solvent solution, $\Delta P_p$, while the pressure drop across the second, or reference capillary, will correspond to the reference liquid, in this case pure solvent, $\Delta P_s$.

The signals generated by the pressure transducers are fed to a differential logarithmic amplifier rather than being linearly subtracted as has been done in the prior art. The differential logarithmic amplifier processes the pressure drop differential as a ratio $\Delta P_p/\Delta P_s$ in real time. Real time signal processing of the simultaneous pressure drops across the analytical and reference capillaries eliminates the effects of flow rate and temperature fluctuations in the capillaries. It also eliminates the need to match the dimensions of the capillaries. The output of the differential logarithmic amplifier is a real time measure of the natural logarithm of the relative viscosity, $\ln \eta_r$.

The pressure drop $\Delta P$ signal generated by the pressure transducer is related to the viscosity of fluid flowing through the capillary in accordance with the following relationship:

$$\Delta P = KQ\eta$$

where
K is the instrument constant which is proportional to the capillary's length l and internal diameter d as follows: $l/d^4$
Q is the volume flow rate
$\eta$ is the effluent liquid viscosity.

When linear subtraction is used as in the prior art, the net signal of the pressure drops across both capillaries is measured as $$\text{Net Signal } (S) = \Delta P_p - \Delta P_s = K_1 Q_1 \eta_p - K_2 Q_2 \eta_s.$$

When the capillaries are arranged in series, the flow rate through each is ideally equal so the net signal equation becomes $$(S) = (K_1 \eta_p - K_2 \eta_s) Q.$$

If the capillaries are matched identically, the foregoing equation will become $$(S) = (\eta_p - \eta_s) K Q.$$

So even under ideal condition, the net signal (S) is still a function of Q and will be affected by the flow rate upsets. Baseline fluctuations and sensitivity variations will also be experienced.

This problem is eliminated when the differential logarithmic amplifier is used since the net signal (S) will be determined as follows:

$$\begin{aligned}(S) &= \ln \Delta P_p - \ln \Delta P_s \\ &= \ln (\Delta P_p/\Delta P_s) \\ &= \ln (G_1 K_1 Q \eta_p/G_2 K_2 Q \eta_s) \\ &= \ln (G_1 K_1 \eta_p/G_2 K_2 \eta_s) \\ &= \ln (G_1 K_1/G_2 K_2) + \ln (\eta_p/\eta_s) \\ &= \ln (G_1 K_1/G_2 K_2) + \ln \eta_r\end{aligned}$$

where as noted earlier $\eta_r$ is the relative viscosity $\eta_p/\eta_s$ and $G_1$ and $G_2$ are the electronic gains in the $\Delta P$ signal measured across the analytical and reference capillary, respectively. The first term is a flow rate and temperature independent instrument constant of the capillary mismatch that can easily be eliminated by suitable zero offset calibration in the instrument electronics. Alternatively, it may be eliminated by matching $G_1 K_1$ to $G_2 K_2$ electronically. The second term is the natural logarithm of the relative viscosity.

By adjusting the gains in each $\Delta P$ signal electronically so as to match $G_1 K_1$ and $G_2 K_2$, the net signal will equal the natural logarithm of the relative viscosity:

$$(S) = \ln \eta_r.$$

This output signal (S) thus will give a direct read out of the inherent and intrinsic viscosities as noted earlier according to the following relationship:

$$\eta_{inh} = \ln (\eta_r)/c$$

$$[\eta] = \lim_{c \to 0} (\ln \eta_r)/c$$

where polymer weight concentration C can be determined by a detector such as the differential refractometer located in the fluid flow path.

The signal output is independent of flow rate and temperature fluctuations and responds only to the polymer viscosity. Moreover, there is no need to match the capillaries.

BRIEF DESCRIPTION OF THE FIGURES

The invention can best be described with reference to the following figures, in which

FIG. 4 is a schematic diagram of a second embodiment of the viscometer when used in connection with GPC analysis.

FIG. 5 is a graph illustrating the signal outputs of the concentration detector and the differential logarithmic amplifier of the GPC-viscometer device of FIG. 4.

FIG. 6 is another graph illustrating the flow rate independence observed in the signal outputs of the differential logarithmic amplifier of the GPC-viscometer device of FIG. 4.

DETAILED DESCRIPTION OF THE PREFERRED EMBODIMENTS

Figure 1:
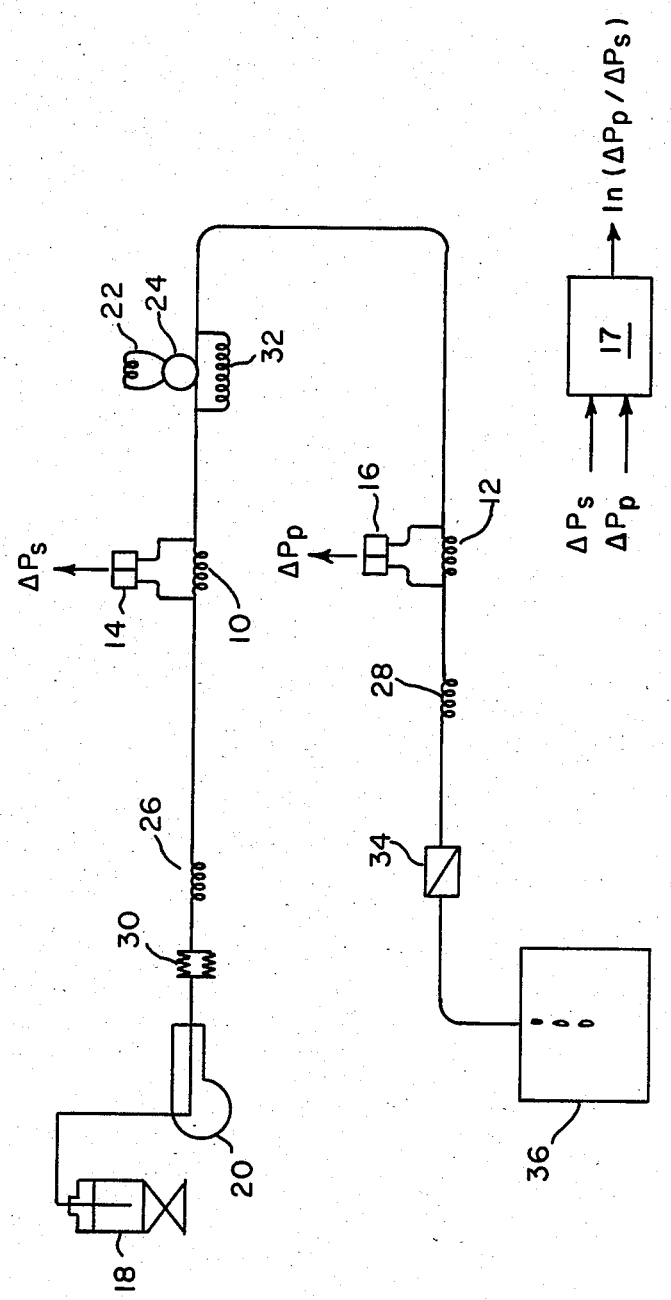
FIG. 1 is a schematic diagram of one embodiment of the viscometer of the present invention.

FIG. 1 illustrates one embodiment of the viscometer of the present invention which can be used in batch sample viscosity determinations. Two capillaries are arranged in series. The first is the reference capillary 10 through which only solvent flows. The second is the analytical capillary 12 through which the polymer-solvent solution will flow. THe capillaries are long tubes of small internal diameter formed of glass, metal or any other suitable material.

Connected across each respective capillary are pressure transducers 14 and 16 which monitor the pressure drops of fluid flowing through the capillaries. Each transducer will generate an electrical signal corresponding to the pressure drop across its capillary. These signals are fed to a differential logarithmic amplifier 17, such as a Burr Brown Log 100 JP.

Solvent is introduced from a reservoir 18 via a pump 20. The polymer sample is injected into the solvent stream from a sample loop 22 via a sample injection valve 24, which may be a two-position 6-port valve. This type of valve is sold by Valco Instruments Inc., under the designation Valco CV6UHPA. The sample loop is located downstream from the reference capillary 10 but before the analytical capillary 12.

Solvent is pumped to the reference capillary through a flow resistor 26 which is a long tube of small internal diameter. This flow resistor and a second flow resistor 28 located downstream from the analytical capillary 12 provide back pressure which improves the performance of the pump 20 and pressure transducers 14 and 16. A pulse dampener 30, which is located between the pump 20 and flow resistor 26, reduces the effect of the pump noise in the signals generated by the transducers.

A third flow resistor 32 provides a solvent flow bypass around the sample injection valve 24. This ensures continuous flow during sample injection and reduces flow rate upsets caused by the valve switching during sample injection.

A concentration detector 34 such as a differential refractometer cell is placed at the end of the stream. Other types of concentration detectors such as ultraviolet or infrared devices may be used depending upon the particular type of sample used. After it passes the concentration detector 34, the sample stream empties into a waste receptacle 36. Where the concentration of the sample is known, a concentration detector is not needed in order to calculate either the inherent or intrinsic viscosity of the polymer.

Figure 2:
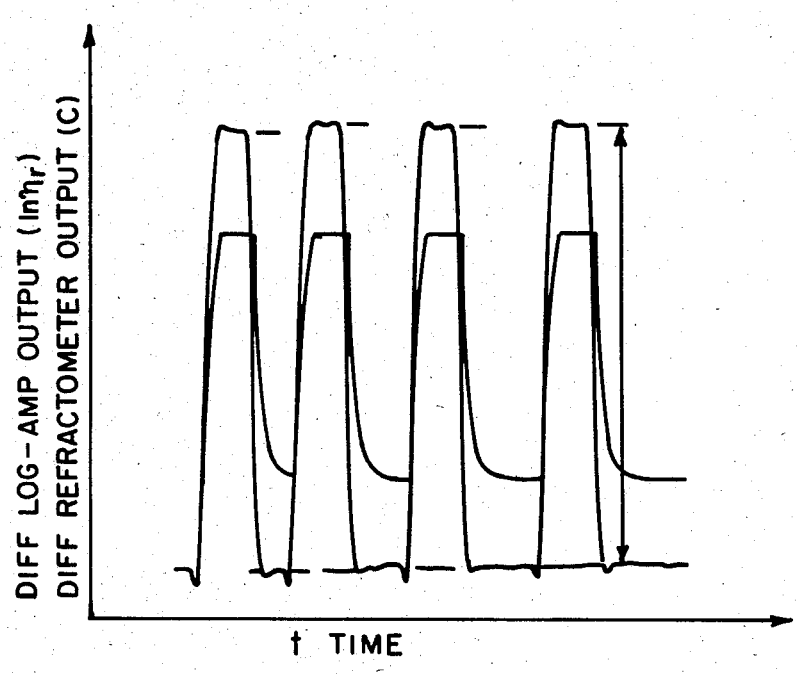
FIG. 2 is a graph illustrating the signal outputs of the concentration detector and differential logarithmic amplifier of the viscometer of FIG. 1.

In operation, the viscometer of FIG. 1 will generate two separate signal detector traces for recording. The signals from pressure transducers 14 and 16 will, by employing a differential logarithmic amplifier, be processed to generate a viscosity (ln $\eta_r$) trace while the concentration detector 34 will generate a concentration C trace. Both will occur simultaneously and repeatedly from successive sample injections as shown in FIG. 2. The sample used to obtain the signal traces of FIG. 2 was polystyrene having a molecular weight of 17,500 in THF solvent at 1 percent weight concentration. From the ln $\eta_r$ and C signals, both the inherent and intrinsic viscosity of the polymer sample can be calculated directly and accurately from the ratio of the signal amplitudes shown in FIG. 2.

Figure 3:
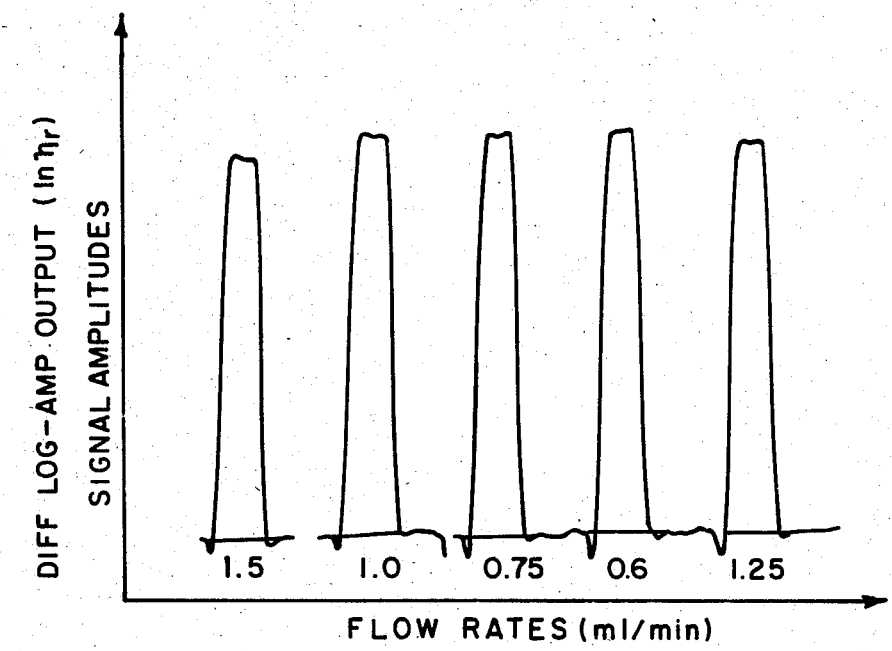
FIG. 3 illustrates the flow rate independence observed in the signal outputs of the differential logarithmic amplifier of the viscometer of FIG. 1.

The flow rate independence of this viscometer has been demonstrated by intentionally varying the flow rate. As shown in FIG. 3, the amplitudes of the viscosity traces remain essentially unchanged as the flow rate is nearly doubled. The sample used in FIG. 3 was polystyrene having a molecular weight of 4000 in THF solvent at 2 percent weight concentration. The middle three amplitude spikes from the output of differential logarithmic amplifier are essentially identically as the flow rate is increased from 0.60 ml/min to 1.0 ml/min. A decrease in amplitude begins to occur as the flow rate is further increased to 1.25 ml/min (right) and 1.5 ml/min (left). In prior art devices, the amplitude of the viscosity signal would have approximately doubled with a doubling in flow rate.

FIG. 4 illustrates a second embodiment of the viscometer of the present invention where like elements are designated by the same reference numerals. The viscometer here is used as a GPC-viscosity detector, but it should be understood that other devices could also be used. A GPC column set 40 is located between the sample loop 22 and injection valve 24 and the analytical capillary 12. It should be noted that the relative positions of the analytical capillary 12 and reference capillary 10 have been reversed in this embodiment. A large depository column 42 has been added and the concentration detector 34 is located between the analytical and reference capillary. Also the flow resistors 28, 26 and 32 have been omitted as has the pulse damper 30. The purpose of column 42 is to dilute the polymer-solvent solution with solvent so that the reference capillary 10 essentially has only solvent passing through it during the detection operation.

While the operation of the GPC-viscosity detector will be described with reference to the schematic of FIG. 4, it should be understood that the viscometer of FIG. 1 could have been used also, modified only by adding a GPC or other SEC column set between the sample injection loop 22 and the analytical capillary 12. Likewise, with the arrangement of FIG. 1, column 42 is not necessary.

A multicomponent polymer mixture sample is injected through sample loop 22 and valve 24. The sample is carried by the solvent and is introduced into the GPC columns 40 where the polymer molecules are separated according to size. The larger molecules are eluted first at the other end as described earlier. The concentration detector 34 detects each polymer component and provides a concentration C signal at the elution time corresponding to each successively smaller molecular weight polymer component.

The $\Delta P$ viscosity detection traces will also occur at the corresponding retention time since each component will generate a pressure drop signal across the analytical capillary 12 as it is eluted from the GPC column set 40.

The $\Delta P$ signals are fed to a differential logarithmic amplifier which will process them as explained above and generate traces corresponding to the natural logarithm of the relative viscosity ln $\eta_r$ of each respective polymer component. These traces occur simultaneously with the GPC concentration traces.

FIG. 5 graphically illustrates these recorded traces for 3-component polystyrene mixture of 0.25 percent weight concentration in THF solvent flowing at the rate of 2 ml/min. The top recording shows the concentration profile of the repeated GPC separation of the 3-component mixture as detected by a differential refractometer. The bottom trace records the same GPC separation, but with the viscometer signal of the log-amplifier output. The viscometer response is shown, as expected, as being highly biased in favoring the detection of the high molecular weight component. The close similarity of the traces for repeat GPC runs demonstrates the good reproducibility of the viscometer for GPC and other SEC applications. This is due to the fine baseline stability as shown in the lower trace which is due in turn to the removal of the dependence on flow rate and temperature upsets and variations.

Flow rate independence is more clearly demonstrated in FIG. 6 in which the same three component polystyrene mixture is used but at slower flow rates. In the traces at the left a flow rate of 1.5 ml/min is used while at the right, 1.0 ml/min. As expected, the separation spreads out with longer elution times at the slower flow rate. The viscosity responses (i.e., the height of the ln ($\eta_r$) traces), however, remain unchanged when the flow rate is slowed from 1.5 to 1.0 ml/min. In the prior art devices, the height would have been reduced by approximately 50% because of flow rate dependency in the signal. This demonstrates how the viscometer of the present invention effectively removes flow rate dependency from measurements made by a capillary type viscometer. A more accurate direct measurement of viscosity is thereby obtained unaffected by any upsets or variations in the flow rates of liquids passing through the viscometer. Moreover, the need for matching exactly the dimensions of the referencing and analytical capillary tubes is also eliminated.

The foregoing also illustrates the independence of the present invention to temperature fluctuations. As noted earlier, temperature control is important in conventional capillary viscometers since small temperature variations in the liquids can greatly affect the accuracy of the viscosity measurements. No special temperature controls are necessary with the present invention. Due to the real time signal processing and the capillary arrangements, temperature fluctuations do not affect the accuracy of the viscosity measurement. This is because the liquid in the analytical and reference capillaries will essentially be at the same temperature each time the relative viscosity signal is processed in real time from the simultaneous pressure drops across each capillary.

While several embodiments and applications of the present invention have been shown and described, it would be apparent to those skilled in the art that many more modifications and applications are possible without departing from the invention, the scope of which is defined by the following claims.

We claim:

1. A method of measuring either the intrinsic or inherent viscosity of a solute in solution with a solvent which is independent of flow rate and temperature fluctuations comprising the steps of:
    passing the solvent through a first capillary tube,
    passing the solution through a second capillary tube connected in series with the first capillary tube,
    measuring separately the pressure drop $\Delta P_s$ across the first capillary tube and the pressure drop $\Delta P_p$ across the second capillary tube when each is full of flowing solvent and solution, respectively,
    generating signals corresponding to the pressure drop across each capillary tube, and
    feeding said signals to a differential logarithmic amplification means which processes the ratio of $\Delta P_p/\Delta P_s$ in real time for use in measuring either the intrinsic or inherent viscosity of the solute wherein the viscosity measured is independent of flow rate and temperature fluctuations.

2. The method of claim 1 which further comprises the steps of measuring the concentration of the solute in the solution passing through the second capillary tube and generating a signal corresponding to the solute concentration.

3. The method of claim 2 wherein the pressure drop across each capillary tube is measured by a pressure transducer and the solute concentration is measured by a differential refractometer.

4. The method of claim 1 wherein the step of passing the solution through the second capillary tube further comprises introducing the solute into the solvent through a valve and providing a restricted solvent flow by-pass around the valve to provide continuous flow during switching of the valve.

5. An apparatus for measuring either the intrinsic or inherent viscosity of a solute in solution with a solvent comprising in combination:
    a first capillary tube through which the solvent flows,
    a second capillary tube arranged in series with the first capillary tube and through which the solution flows,
    solvent supply means for supplying solvent to flow through both capillary tubes,
    solution supply means for introducing a sample of the solute in solution with the solvent to flow through the second capillary tube,
    means for measuring the pressure drop $\Delta P_s$ across the first capillary tube and the pressure drop $\Delta P_p$ across the second capillary tube and generating a signal responsive to each pressure drop, and
    logarithmic amplification means for receiving and processing in real time the ratio of pressure drop signals of $\Delta P_p/\Delta P_s$ for use in measuring either the intrinsic or inherent viscosity of the solute independent of the flow rate and temperature fluctuations of the solution and the solvent.

6. The apparatus of claim 5 further comprising means for measuring the concentration of the solute in the solution flowing through the second capillary tube and generating a signal responsive thereto.

7. The apparatus of claim 6 wherein the means for measuring pressure drop across each capillary tube comprises a pressure transducer and the means for measuring solute concentration comprises a differential refractometer.

8. The apparatus of claim 5 wherein the solvent supply means comprises a reservoir of solvent and a pump with a pulse dampener to reduce pumping noise in the fluid flow.

9. The apparatus of claim 5 wherein the solution supply means comprises a valve for introducing the solute sample and a restricted flow by-pass around the valve to provide continuous solvent flow during switching of the valve.

10. The apparatus of claim 5 further comprising a flow resistor before the first capillary tube and a flow resistor after the second capillary tube.

11. A method of determining the molecular weight distribution of polymer materials as they are eluted from a size exclusion chromatographic column means by a solvent comprising the steps of:
    passing solvent through the size exclusion chromatographic column means and through a first and second capillary tubes arranged in series,
    introducing a sample of polymer materials into the solvent before said column means so that a polymer material-solvent solution flows into the column means,
    passing the solution through the first capillary tube after it is eluted from said column means,
    measuring the pressure drop $\Delta P_s$ across the second capillary tube when it is full of flowing solvent,
    measuring the pressure drop $\Delta P_p$ across the first capillary tube as the polymer materials eluted from said column means pass through the first capillary tube,
    measuring the concentrations of the polymer materials that are eluted from said column means,
    generating signals corresponding to the pressure drop and concentration measurements, and feeding said signals to a differential logarithmic amplification means which processes the ratio of $\Delta P_p/\Delta P_s$ in real time for use in calculating either the intrinsic or inherent viscosities of the polymer materials that are eluted from the column means wherein the viscosity calculated is independent of flow rate and temperature fluctuations and determining molecular weight distribution of the polymer materials.

12. The method of claim 11 wherein the step of passing the sample through the column means further comprises introducing the sample into the solvent through a valve and providing a restricted solvent flow by-pass around the valve to provide continuous flow during switching of the valve.

13. The method of claim 11 wherein a dilution means is employed between the capillary tubes to ensure that essentially only solvent flows through the second capillary tube while the pressure drops across both capillary tubes are being measured.

14. An apparatus for determining the molecular weight distribution of polymer materials as they are eluted from a size exclusion chromatographic column means by a solvent comprising in combination:
   first and second capillary tubes arranged in series, wherein solvent flows through the second capillary tube and a polymer material-solvent solution flows through the first,
   solvent supply means for supplying solvent to flow through both capillary tubes and the column means,
   solution supply means for introducing a sample of the polymer materials, the supply means located at the entrance end of the column means and the first capillary tube located at the exit end of the column means,
   means for measuring the pressure drop $\Delta P_p$ across the first capillary tube as the polymer materials are eluted from the column means and pass through the first capillary tube,
   means for measuring pressure drop $\Delta P_s$ across the second capillary when it is full of flowing solvent,
   means for measuring the concentration of the polymer materials that are eluted from said column means,
   means for generating signals corresponding to the pressure drop and concentration measurements, and
   logarithmic amplification means for receiving and processing in real time the ratio of pressure drop signals of $\Delta P_p/\Delta P_s$ and means for employing the concentration signal to determine the molecular weight distribution of the polymer materials that are eluted from the column means by measuring either the intrinsic or inherent viscosities of the polymer materials independent of the flow rate and temperature fluctuations.

15. The apparatus of claim 14 wherein the solvent supply means comprises a reservoir of solvent and a pump with a pulse dampener to reduce pumping noise in the fluid flow.

16. The apparatus of claim 15 wherein the solution means comprises a valve for introducing the sample and a restricted flow by-pass around the valve to provide continuous solvent flow during switching of the valve.

17. The apparatus of claim 15 wherein the means for measuring the pressure drops across each capillary tube comprises a pressure transducer and the means for measuring sample concentration comprises a differential refractometer.

18. The apparatus of claim 15 further comprising a flow resistor before the first capillary tube and a flow resistor after the second capillary tube.

19. The apparatus of claim 15 wherein a concentration dilution means is located between the capillary tubes to ensure that essentially only solvent flows through the second capillary tube while the pressure drops across both capillary tubes are being measured.

20. A method of measuring the viscosity of a sample liquid which is independent of flow rate and temperature fluctuations comprising the steps of:
   passing a reference liquid through a first capillary tube,
   passing the sample liquid through a second capillary tube connected in series with the first capillary tube,
   measuring separately the pressure drop $\Delta P_r$ across the first capillary tube when it is full of flowing reference liquid and the pressure drop $\Delta P_p$ across the second capillary tube when it is full of flowing sample liquid,
   generating signals corresponding to the pressure drop across each capillary tube, and feeding said signals to a differential logarithmic amplifications means which processes the ratio of $\Delta P_p/\Delta P_r$ in real time for use in measuring the relative viscosity of the two liquids whereby the viscosity of the sample can be determined independent of flow rate and temperature fluctuations.

21. The method of claim 20 wherein the reference liquid is a solvent for the sample liquid.

22. The method of claim 20 wherein the viscosity of the reference liquid is known.

23. An apparatus for measuring the viscosity of a sample liquid which is independent of flow rate and temperature fluctuations comprising in combination:
   a first capillary tube through which a reference liquid flows,
   a second capillary tube arranged in series with the first capillary tube and through which the sample liquid flows,
   means for measuring the pressure drop $\Delta P_r$ across the first capillary tube and means for measuring the pressure drop $\Delta P_p$ across the second capillary tube generating a signal responsive to each pressure drop, and
   logarithmic amplification means for receiving and processing the ratio of the pressure drop signals $\Delta P_r/\Delta P_s$ in real time so as to determine the relative viscosity of the two liquids independent of the flow rate and temperature fluctuations.

24. The apparatus of claim 23 wherein the reference liquid is a solvent for the sample liquid.

25. The apparatus of claim 6 wherein the viscosity of the reference liquid is known.

* * * * *